US00PP29691P3

(12) United States Plant Patent
Miyazaki

(10) Patent No.: US PP29,691 P3
(45) Date of Patent: Sep. 18, 2018

(54) ***PETUNIA* PLANT NAMED 'SURF GOREHANA'**

(50) Latin Name: *Petunia x hybrida*
Varietal Denomination: Surf Gorehana

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 24 days.

(21) Appl. No.: 15/530,375

(22) Filed: Jan. 4, 2017

(65) Prior Publication Data

US 2018/0192567 P1 Jul. 5, 2018

(51) Int. Cl.
*A01H 5/02* (2018.01)

(52) U.S. Cl.
USPC ..... Plt./356.23

(58) Field of Classification Search
USPC ..... Plt./356.23
See application file for complete search history.

*Primary Examiner* — Anne Marie Grunberg
(74) *Attorney, Agent, or Firm* — C. A. Whealy

(57) ABSTRACT

A new and distinct cultivar of *Petunia* plant named 'Surf Gorehana', characterized by its outwardly trailing plant habit; vigorous growth habit; freely branching habit; freely flowering habit; long flowering period; medium to large flowers that are bright red in color; and good garden performance.

1 Drawing Sheet

Botanical designation: *Petunia* x *hybrida*.
Cultivar denomination: 'SURF GOREHANA'.

BACKGROUND OF THE INVENTION

The present invention relates to a new and distinct cultivar of *Petunia* plant, botanically known as *Petunia* x *hybrida* and hereinafter referred to by the name 'Surf Gorehana'.

The new *Petunia* plant is a product of a planned breeding program conducted by the Inventor in Higashiomi, Shiga, Japan. The objective of the breeding program is to create new trailing and freely-flowering *Petunia* plants with medium to large attractive flowers.

The new *Petunia* plant originated from a cross-pollination made by the Inventor in July, 2013 in Higashiomi, Shiga, Japan of a proprietary selection of *Petunia* x *hybrida* identified as code designation PV500-5, not patented, as the female, or seed, parent with a proprietary selection of *Petunia* x *hybrida* identified as code designation PV508-2, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in July, 2014.

Asexual reproduction of the new *Petunia* plant by terminal vegetative cuttings in a controlled greenhouse environment in Higashiomi, Shiga, Japan since January, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf Gorehana'. These characteristics in combination distinguish 'Surf Gorehana' as a new and distinct *Petunia* plant:

1. Outwardly trailing plant habit.
2. Vigorous growth habit.
3. Freely branching habit.
4. Freely flowering habit.
5. Long flowering period.
6. Medium to large flowers that are bright red in color.
7. Good garden performance.

Plants of the new *Petunia* can be compared to plants of the female parent selection. Plants of the new *Petunia* differ primarily from plants of the female parent selection in flower color as plants of the female parent selection have carmine-colored flowers. In addition, plants of the new *Petunia* are more trailing in plant habit than plants of the female parent selection.

Plants of the new *Petunia* can be compared to plants of the male parent selection. Plants of the new *Petunia* differ primarily from plants of the male parent selection in growth habit as plants of the new *Petunia* are more vigorous than and not as compact as plants of the male parent selection.

Plants of the new *Petunia* can also be compared to plants of the *Petunia* x *hybrida* 'Sunsurf Akatora', disclosed in U.S. Plant Pat. No. 23,970. In side-by-side comparisons, plants of the new *Petunia* and 'Sunsurf Akatora' differ primarily in the following characteristics:

1. Plants of the new *Petunia* are broader than plants of 'Sunsurf Akatora'.
2. Plants of the new *Petunia* have longer lateral branches than plants of 'Sunsurf Akatora'.
3. Plants of the new *Petunia* have broader leaves with thicker petioles than plants of 'Sunsurf Akatora'.
4. Plants of the new *Petunia* are more freely flowering than plants of 'Sunsurf Akatora'.
5. Flowers of plants of the new *Petunia* are larger than flowers of plants of 'Sunsurf Akatora'.

6. Flower petals of plants of the new *Petunia* are more undulate than flower petals of plants of 'Sunsurf Akatora'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Surf Gorehana' grown in a container.

The photograph at the bottom of the sheet is a close-up view of a typical flowering plant of 'Surf Gorehana'.

DETAILED BOTANICAL DESCRIPTION

The aforementioned photographs and following observations, measurements and values describe plants grown during the early summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Petunia* x *hybrida* 'Surf Gorehana'.

Parentage:

- *Female, or seed, parent*.—Proprietary selection of *Petunia×hybrida* identified as code designation PV500-5, not patented.
- *Male, or pollen, parent*.—Proprietary selection of *Petunia×hybrida* identified as code designation PV508-2, not patented.

Propagation:

- *Type*.—By terminal vegetative cuttings.
- *Time to initiate roots, summer and winter*.—About one week at temperatures about 15° C. to 20° C.
- *Time to produce a rooted young plant, summer and winter*.—About three weeks at temperatures about 15° C. to 20° C.
- *Root description*.—Fibrous; typically white in color, actual color of the roots is dependent on substrate composition, water quality, fertilizer type and formulation, substrate temperature and physiological age of roots.
- *Rooting habit*.—Freely branching; dense.

Plant description:

- *Plant form and growth habit*.—Outwardly trailing plant habit; freely branching habit with numerous lateral branches developing per plant; pinching enhances lateral branch development; vigorous growth habit.
- *Plant height*.—About 19 cm.
- *Plant diameter*.—About 68 cm.

Lateral branch description:

- *Length*.—About 29 cm.
- *Diameter*.—About 2.5 mm.
- *Internode length*.—About 2.3 cm.
- *Strength*.—Strong, flexible.
- *Aspect*.—Mostly outwardly.
- *Texture*.—Pubescent; rough; viscid.
- *Color*.—Close to 144B.

Leaf description:

- *Arrangement*.—Alternate, simple.
- *Length*.—About 4.75 cm.
- *Width*.—About 2.8 cm.
- *Shape*.—Elliptic.
- *Apex*.—Broadly acute.
- *Base*.—Attenuate.
- *Margin*.—Entire; undulate.
- *Texture, upper and lower surfaces*.—Sparsely pubescent; rough; viscid.
- *Venation pattern*.—Pinnate; reticulate.
- *Color*.—Developing leaves, upper surface: Close to 137C. Developing leaves, lower surface: Close to 144A. Fully expanded leaves, upper surface: Close to 137B; venation, close to 145A. Fully expanded leaves, lower surface: Close to 146B; venation, close to 145A.
- *Petioles*.—Length: About 5.1 mm. Diameter: About 3.7 mm. Texture, upper and lower surfaces: Sparsely pubescent; rough. Color, upper and lower surfaces: Close to 145A.

Flower description:

- *Flower arrangement and habit*.—Single-type salver-form flowers arising from upper leaf axils; freely flowering habit with usually about 60 to 70 flowers developing per plant; flowers face mostly upright to outwardly.
- *Fragrance*.—None detected.
- *Natural flowering season*.—Early flowering habit; plants of the new *Petunia* initiate and develop flowers about three to four weeks after planting; long flowering period, flowering commences naturally during the spring and plants flower continuously throughout the summer until late autumn in Japan.
- *Flower longevity*.—Individual flowers last about seven to ten days on the plant; flowers not persistent.
- *Flower buds*.—Length: About 4.6 cm. Diameter: About 1.1 cm. Shape: Cylindrical. Color: Close to 184D; towards the apex, close to 182B; towards the base, close to 199D.
- *Flower diameter*.—About 6.3 cm.
- *Flower length (depth)*.—About 2 cm.
- *Flower tube length*.—About 3.2 cm.
- *Flower tube diameter, proximally*.—About 4.2 mm.
- *Flower tube diameter, distally*.—About 1.4 cm.
- *Corolla*.—Quantity and arrangement: Five in a single whorl, fused at the base and opening into a flared trumpet. Petal length from throat: About 2.3 cm. Petal width: About 2.7 cm. Petal shape: Roughly spatulate. Petal apex: Cuspidate. Petal margin: Entire, lobed; undulate. Petal texture, upper and lower surfaces: Smooth, glabrous; velvety. Throat texture: Smooth, glabrous. Tube texture: Pubescent. Color: Petal, when opening, upper surface: Close to 46A. Petal, when opening, lower surface: Close to 51B to 51C. Petal, fully opened, upper surface: Close to 46A; venation, close to 178A; color does not change with development. Petal, fully opened, lower surface: Close to 51C; midvein, close to 56D; color does not change with development. Throat: Distally, close to 47B; center, close to 49D; proximally, close to 145D; venation, close to 166A. Tube: Distally, close to 75C; center, close to 162D; proximally, close to 145D.

*Calyx*.—Arrangement: One star-shaped calyx tube with five sepals in a single whorl and fused at the base. Sepal length: About 1.7 cm. Sepal width: About 3.4 mm. Sepal shape: Lanceolate. Sepal apex: Acute. Sepal margin: Entire. Sepal texture, upper and lower surfaces: Pubescent; viscid. Color, upper surface: Close to 137B. Color, lower surface: Close to 146B.

*Peduncles*.—Length: About 1.3 cm. Diameter: About 1.5 mm. Strength: Strong, flexible. Aspect: Upright to outwardly. Texture: Pubescent, rough; viscid. Color: Close to 144B.

*Reproductive organs*.—Stamens: Quantity per flower: Five. Filament length: About 1.9 cm. Filament color: Close to 155C. Anther shape: Ellipsoidal. Anther size: About 2.1 mm by 2.3 mm. Anther color: Close to NN155A. Pollen amount: Abundant. Pollen color: Close to NN155D. Pistils: Quantity per flower: One. Pistil length: About 2.2 cm. Style color: Close to 145D. Stigma shape: Transversely ellipsoidal. Stigma color: Close to 145C. Ovary color: Close to 144A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Surf Gorehana' as illustrated and described.

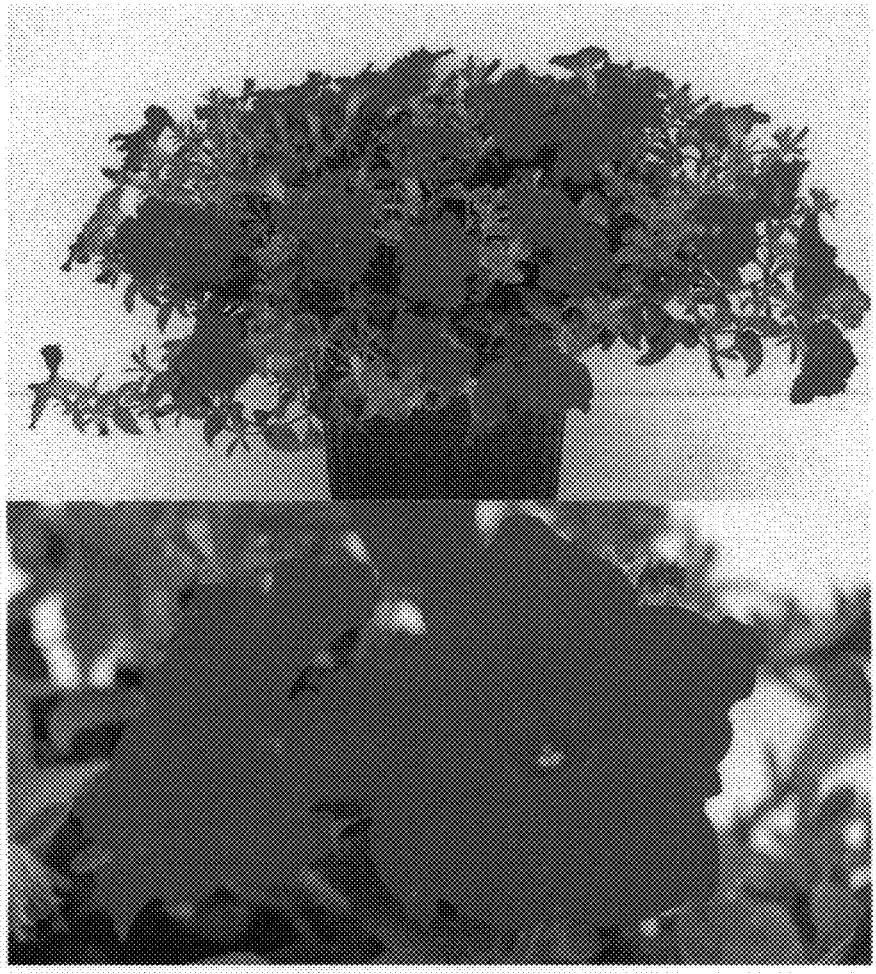

* * * * *